United States Patent [19]
Richter et al.

[11] 4,262,141
[45] Apr. 14, 1981

[54] PREPARATION OF ALDEHYDES

[75] Inventors: Wolfgang Richter, Ludwigshafen; Rudolf Kummer, Frankenthal; Kurt Schwirten, Ludwigshafen, all of Fed. Rep. of Germany

[73] Assignee: BASF Aktiengesellschaft, Fed. Rep. of Germany

[21] Appl. No.: 69,919

[22] Filed: Aug. 27, 1979

[30] Foreign Application Priority Data

Sep. 15, 1978 [DE] Fed. Rep. of Germany ....... 2840168

[51] Int. Cl.$^3$ ............................................. C07C 45/50
[52] U.S. Cl. ................................................... 568/454
[58] Field of Search ....................... 260/604 HF, 909; 568/454, 451

[56] References Cited

U.S. PATENT DOCUMENTS

| | | | |
|---|---|---|---|
| 3,555,098 | 1/1971 | Oliver | 260/604 HF |
| 3,839,459 | 10/1974 | Bennett et al. | 260/604 HF |
| 3,875,240 | 4/1975 | McClure | 260/604 HF |
| 4,049,725 | 9/1977 | Gueant et al. | 260/604 HF |

FOREIGN PATENT DOCUMENTS

2730527 12/1978 Fed. Rep. of Germany .... 260/604 HF

*Primary Examiner*—Werren B. Lone
*Attorney, Agent, or Firm*—Keil & Witherspoon

[57] ABSTRACT

Aldehydes are prepared by hydroformylating the corresponding olefinically unsaturated compounds with the aid of rhodium-carbonyl complexes which contain tertiary phosphines as ligands, by carrying out the reaction in the presence of compounds of copper, silver or zinc which are soluble in the reaction mixture and do not contain any component which deactivates the rhodium-carbonyl complexes.

5 Claims, No Drawings

PREPARATION OF ALDEHYDES

The present invention relates to an improved process for the preparation of aldehydes by hydroformylating the corresponding olefinically unsaturated compounds with the aid of rhodium-carbonyl complexes which contain tertiary phosphines as ligands.

The hydroformylation of olefinically unsaturated compounds with the aid of cobalt-carbonyl or rhodium-carbonyl complexes as CO transfer catalysts is a generally known reaction.

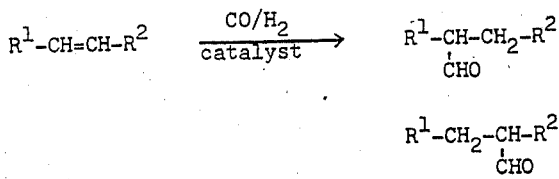

$R^1$ and $R^2$ are H or organic radicals.

Further, it is generally known that the use of rhodium-carbonyl complexes which contain tertiary phosphines as ligands offer particular advantages in respect of the outcome of the process, and in technological respects. One of these advantages is that the said catalysts are very heat-stable even under atmospheric pressure so that the products can be distilled from the reaction mixture without the catalysts undergoing decomposition. The catalysts remain in the high-boiling residue, which can be recycled to the hydroformylation stage.

Since the amount of residue in this way naturally constantly increases, it is periodically necessary to treat it, for example by heating it with an aqueous peroxide and nitric acid and reconverting the rhodium salts, which hereupon substantially pass into the aqueous phase, into the active complexes, or their intermediates, by conventional methods. It is obvious that these and similar treatments, for example by extraction or combustion, are troublesome and expensive subsidiary operations which it is desirable to avoid, or at least limit, as far as possible. It is therefore all the more disadvantageous that treatment of the residue not only becomes necessary when the amount of residue becomes unacceptably large, but also because in the course of about 1,000 operating hours the activity of the catalyst drops to a value below which the hydroformylation becomes uneconomical, since the reaction time required becomes too long.

The reasons for the loss of activity largely remain to be clarified in detail, but it can be assumed that what is involved in every case is a displacement of the mobile carbonyl groups by more stable ligands, so that CO transfer is no longer possible. This assumption is, for example, in agreement with the fact that the cyanide group, which is a particularly stable ligand, is a correspondingly powerful catalyst poison. To a lesser extent this also applies to halogen ions and sulfide ions.

It is an object of the present invention to preserve the activity of the catalyst to the extent that treatment of the high-boiling catalyst-containing residues because of decreasing activity is no longer necessary.

We have found that this object is achieved in an improved process for the preparation of aldehydes by hydroformylating the corresponding olefinically unsaturated compounds with the aid of rhodium-carbonyl complexes which contain tertiary phosphines as ligands, wherein the reaction is carried out in the presence of compounds of copper, silver or zinc which are soluble in the reaction mixture and do not contain any component which deactivates the rhodium-carbonyl complexes.

Further, it has been found that compounds of copper and zinc are particularly suitable for the above purpose. As compounds of the said metals which accord with the above definition it is possible to use salts, oxides and complexes, with the exception of those compounds whose components have a deactivating effect on the rohodium catalyst. Accordingly, for example, the halides, sulfides and cyanides are, as is self-evident, unsuitable. On the other hand suitable compounds are, inter alia, the sulfates and phosphates and above all the fatty acids salts, such as the acetates, propionates, butyrates or stearates. The oxides or hydroxides can also be employed since, under the reaction conditions, these are converted by the organic acids, always present in the hydroformylation mixture, into the salts of these acids. Further, complex compounds such as the acetylacetonates and acetoacetates are also very suitable.

Whether a compound is suitable can be readily determined by simple model experiments, wherein a test hydroformylation is carried out in the presence of a rhodium catalyst which has been completely deactivated with sulfide or chloride; in that case, the rate of reaction is virtually zero, i.e. no conversion of olefin to aldehyde takes place. A compound of one of the above metals is considered suitable if, after addition of the compound, the hydroformylation reaches—possibly after a short induction period—the rate of reaction which is achieved with a fresh Rh catalyst which has not been deactivated. The rate of reaction in this experiment can easily be determined from the consumption of the $CO/H_2$ gas mixture. However, it should be emphasized that apart from a few classes of compounds (for example halides, cyanides and sulfides), most compounds of the above metals do fulfill the purpose according to the invention. Presumably, the metal compounds act by virtue of the fact that the metals in question have a greater difficulty for the inhibiting substances, for example halides, sulfides and cyanides, than does rhodium. Accordingly, the amount of the active metal compounds—which is advantageously always expressed in terms of the amount of metal—depends on the amount of the inhibiting substances. Since, in most cases, very small amounts are involved and since furthermore the nature of the inhibitors is not precisely known, this effective amount must be determined empirically from case to case. However, according to observations made hitherto an excess of the metal compound is not detrimental.

As a general rule for hydroformylations of olefins of conventional technical purity, the atomic ratio of rhodium to one of the metals mentioned should be from 1:0.1 to 1:20, from which the amount of metal compound can be calculated. This amount suffices to ensure the undiminished activity of the rhodium catalyst for about 4,000 operating hours, i.e. approximately for the length of time after which catalyst regeneration in any case becomes necessary for the purpose of removing the high-boiling residue which by then has accumulated in the circulation system.

If the catalyst regeneration is carried out by boiling the residue with an aqueous mixture of nitric acid and hydrogen peroxide, not only does the rhodium pass into the aqueous phase as rhodium nitrate, but so does the additional metal used, again as its nitrate.

Using a tertiary phosphine in the presence of $H_2$ and CO at 1-5 bar, the rhodium complex can hereupon be precipitated and is then recycled to the hydroformylation stage. Unless it is more economical to discard the residual metal nitrate solutions, the nitrates can be isolated by evaporation and can, if desired, then be converted by heating into the oxides, after which the oxides can be dissolved in an organic acid and the resulting solutions can also be recycled.

The success of the process according to the invention is independent of the nature of the hydroforymlation, that is to say of the nature of the olefin employed, so that it is superfluous to enumerate the processes employed or feasible for the purpose. However, the process is naturally of special importance in the large-scale synthesis of industrial chemicals, for example in the hydroformylation of propylene to n-butyraldehyde (and, in addition, iso-butyraldehyde) and the hydroformylation of ethylene to propionaldehyde, since in these reactions extreme economy is important. In general, the hydroformylation by means of the rhodium catalyst is carried out at a pressure of 1-30 bar and at from 70° to 150° C., using an equimolar, or about equimolar, mixture of CO and $H_2$.

The preferred rhodium catalysts have the general formula $HRh(CO)(PR_3)_3$ where the radicals R, which may be identical or different, are hydrocarbon radicals of 4 to 12 carbon atoms. For industrial purposes, phenyl (Ph) is a particularly important radical R, and triphenylphosphine ($PPh_3$) a particularly important ligand. However, the nature of the tertiary phosphine has in other respects no recognizable influence on the process improvement according to the invention. The rhodium may be employed in the form of the complex mentioned, or in the form of a rhodium salt, eg. rhodium nitrate, together with a corresponding amount of the phosphine. In this latter case, the active complex forms in situ under the hydroformylation conditions. Further, it is at times advantageous to employ the phosphine in an excess of up to 100 times the stoichiometric amount.

The concentration of catalyst, expressed as metal, is from 10 to 1,000 ppm of the reaction mixture, as is conventionally the case with Rh-catalyzed hydroformylation.

EXAMPLE 1

In a series of experiments, 80 g portions of oct-1-ene, dissolved in 250 ml of toluene, were hydroformylated in an autoclave of 2 liters capacity, in the presence of 2 g of triphenylphosphine and 5 mg of rhodium in the form of the complex $HRh(CO)(PPh_3)_3$, at 100° C. under a pressure of 10 bar, employing an equimolar $CO/H_2$ mixture, the reaction being carried out.

(a) with a freshly prepared catalyst,
(b) with a catalyst which was contained in 8 g of a high-boiling residue originating from the hydroformylation of ethylene,
(c) with a catalyst solution (b) which additionally contained 100 mg of Cu (II) acetylacetonate (Rh:Cu=1:8) and
(d) with a catalyst solution (b) which additionally contained zinc acetylacetonate (Rh:Zn=1:8).

In case (a), no further gas was absorbed after 1.5 hours, i.e. after this time virtually 100% conversion had been reached. During this same time, a conversion of only about 50% was found with catalyst (b). In the case of the catalyst system employing copper (case c), the conversion was also virtually complete, whilst with zinc (case d) this optimum result was not quite achieved within the same time, the conversion being about 95%.

EXAMPLE 2

In a model experiment under the same conditions as in Example 1, the Rh complex referred to there was replaced by the complex $ClRh(CO)(PPh_3)_2$, used
(a) alone,
(b) in the presence of copper nonanate and
(c) in the presence of zinc nonanate.

After 1.5 hours, a conversion of only 10% was achieved in case (a), whilst it was virtually 100% in cases (b) and (c), as in Example 1.

The same picture emerged on using the catalyst $HRh(CO)(PPh_3)_3$, which was exposed to the action of hydrogen chloride before use.

EXAMPLE 3

The catalyst $HRh(CO)(PPh_3)_3$, treated with hydrogen sulfide before use, was employed in a model experiment using the same conditions and molar ratios as in Example 1. This deactivated catalyst was
(a) used alone and
(b) used together with copper II acetylacetonate.

In case (a), virtually no conversion occurred, whilst in case (b) the reaction started after a short induction period and reached about 100% conversion after 1.7 hours.

We claim:

1. In a hydroformylation process in which an olefinically unsaturated compound is reacted with a gaseous mixture of hydrogen and carbon monoxide in the presence of an effective amount of a rhodium-carbonyl complex catalyst containing tertiary phosphines as ligands to form a corresponding aldehyde, the improvement which comprises:
maintaining the activity of the rhodium-carbonyl complex catalyst for an extended period of time by carrying out the hydroformylation reaction in the presence of an effective amount of a compound of copper, silver or zinc which is soluble in the reaction mixture and which does not contain a component which deactivates the rhodium-carbonyl complex catalyst.

2. A process for the preparation of an aldehyde as set forth in claim 1 wherein the atomic ratio of rhodium to copper, silver or zinc is from about 1:0.1 to 1:20.

3. A process for the preparation of aldehydes as set forth in claim 1 wherein said catalyst has the general formula $HRh(CO)(PR_3)_3$, where the radicals which may be identical or different, are hydrocarbon radicals of 4 to 12 carbon atoms.

4. A process for the preparation of an aldehyde as set forth in claims 1 or 2 wherein said hydroformylation reaction is carried out in the presence of an effective amount of at least one fatty acid salt of copper, silver or zinc which is soluble in the reaction mixture and does not contain a component which deactivates the rhodium-carbonyl complexes.

5. A process for the preparation of an aldehyde as set forth in claim 1 wherein said catalyst comprising rhodium-carbonyl complexes contains triphenylphosphine as a ligand.

* * * * *